(12) United States Patent
Getty et al.

(10) Patent No.: US 7,667,043 B2
(45) Date of Patent: Feb. 23, 2010

(54) MOLECULAR STRUCTURES WITH CONTROLLABLE ELECTRON CONDUCTING PROPERTIES

(75) Inventors: Ross Getty, Wilmington, DE (US); Simona Percec, Philadelphia, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/384,807

(22) Filed: Mar. 20, 2006

(65) Prior Publication Data

US 2007/0215866 A1    Sep. 20, 2007

(51) Int. Cl.
*C07D 213/02*    (2006.01)
*C07C 327/00*    (2006.01)
(52) U.S. Cl. ...................... 546/285; 558/251
(58) Field of Classification Search .............. 546/276.4, 546/313, 285; 548/427; 585/26; 558/251
See application file for complete search history.

(56) References Cited

U.S. PATENT DOCUMENTS 6,430,511 B1    8/2002  Tour et al.
2005/0084711 A1*  4/2005  Sasaki et al. ................ 428/690

FOREIGN PATENT DOCUMENTS

EP    0 521 360 B1    1/1993
WO   WO 00/44094 A1   7/2000

OTHER PUBLICATIONS

Park et al, 1998, Tetrahedron, 54(42), p. 12707-12714.*
Becket et al. "On-Chain Fluorenone Defect Emission from Single Polyfluorene Molecules in the Absence of Intermolecular Interactions" Advanced Functional Materials, 2006, vol. 16, No. 3, pp. 364-370.*
J. Chen et al., Large On-Off Ratios and Negative Differential Resistance in a Molecular Electronic Device, Science, vol. 286(5444):1550-1556, 2004.
Robert M. Metzger, All About (N-Hexadecylquinolin-4-ium-1-yl)Methylidenetricyanoquinodimethanide, A Unimolecular Rectifier of Electrical Current, J. Mater. Chem., vol. 10:55-62, 2000.
C. P. Collier et al., Electronically Configurable Molecular-Based Logic Gates, Science, vol. 285(5426):391-399, 2004.
Eric W. Wong et al., Fabrication and Transport Properties of Single-Molecule-Thick Electrochemical Junctions, J. Am. Chem. Sco., vol. 122:5831-5840, 2000.
James M. Tour, Molecular Electronics, Synthesis and Testing of Components, Acc. Chem. Res., vol. 33:791-804, 2000.
L. A. Bumm et al., Are Single Molecular Wires Conducting?, Science, vol. 271;1705-1707, Mar. 22, 1996.
Mikael Trollsas et al., Synthesis of Novel Sulfonyl-Containing Liquid-Crystalline Side-Chain Poly(Vinyl Ethers), Macromol. Chem. Phys., vol. 196:1821-1837, 1995.
Zhengguo Zhu et al., Synthesis and Characterization of Monodendrons Based on 9-Phenylcarbazole, J. Org. Chem., vol. 65:116-123, 2000.
Leopoldo Della Ciana et al., Synthesis of 1,4-Bis(4-Pyridyl)Butadiyne, J. Heterocyclic Chem., vol. 27:607-608, 1984.
Jeffery A. Whiteford et al., Molecular Architecture Via Coordination: Self-Assembly, Characterization, and Host-Guest Chemistry of Mixed, Neutral-Charged, Pt-Pt and Pt-Pd Macrocyclic Tetranuclear Complexes. X-Ray Crystal Structure of Cyclobis[[Cis-Pt(DPPP)(4-Ethynylpyridine)2][Cis-Pd2+(Pet3)22-OSO2CF3]], J. Am. Chem. Soc., vol. 119:2524-2533, 1997.

* cited by examiner

*Primary Examiner*—Rebecca L Anderson
*Assistant Examiner*—Joseph R Kosack

(57) ABSTRACT

Aromatic and heteroaromatic molecular structures with controllable electron conducting properties are derived from the incorporation of electron active substituents in selective positions. Such compounds can form self-assembled layers on metal or other substrates, and can be used in molecular scaled opto-electronic devices including field-effect transistors, light-emitting diodes and photovoltaic cells.

3 Claims, No Drawings

MOLECULAR STRUCTURES WITH CONTROLLABLE ELECTRON CONDUCTING PROPERTIES

FIELD OF INVENTION

The invention is directed to the preparation of novel aromatic and heteroaromatic molecular structures with controllable electron conducting properties, useful for the synthesis of molecular wires and/or molecular switches

BACKGROUND

With the expanding commercial interest in the generation of small nano-scale electronic devices there is a need for the generation of a new class of conductive molecules that are functionalized to be adaptable for nano-device fabrication. However, the discovery of new and improved conductive molecules for use in nano-electronic devices is hampered by a number of problems. Little is known about the specifics of how conductive molecules work. Additionally, it is difficult to connect conductive molecules to electrodes and even more difficult to perform conductivity measurements on single molecules. The coupling of different aromatic and heteroaromatic building blocks is difficult to achieve because substituted structures are prone to side reactions and long reaction times.

In spite of these difficulties a number of conductive molecules have been synthesized. For example, Tour et al (WO 00/01360) teaches the assembly of molecular structures consisting of phenylene/ethynylene units and the measurement of the resistance/conductivity of a self-assembled monolayer deposited on a pattern of electrodes. Molecular structures consisting of phenylene/ethynylene units have been already suggested in the literature to function as molecular wires or switches (S. J. Tour, *Acc. Chem Res.*, 2000, 33, 791). Very few of these structures have been demonstrated to display distinct negative differential resistance (NDR) (increased resistance with increasing driving voltage) and then only under specific conditions, mostly at low temperatures.

Additionally, several groups (J. Chen et al, *Science*, 1999, 286, 1550; E. W. Wong et al, *J. Am. Chem. Soc.*, 2000, 122, 5821-5840) have synthesized conducting molecules and measured the negative differential resistance behavior and conductivity of a monolayer of this material between two surfaces. C. P. Collier et al, (*Science*, 1999, 285, 391) have synthesized rotaxane and catenane molecules, made monolayers of these molecules using Langmuir-Blogett techniques, and demonstrated resonant tunneling current flow derived from the reversible inter-conversion between two different electronic states.

Commonly owned US-2004/0138467 discloses aromatic and aromatic/heteroaromatic molecular structures with controllable electron conducting properties which are derived from the incorporation of electron active substituents in selective positions.

The above listed references teach the synthesis of useful compounds, however they do not address the need for functionalized molecules specifically adapted for facile nano-device fabrication.

SUMMARY OF THE INVENTION

The invention relates to development of new aromatic and heteroaromatic conducting molecules for use in the synthesis of three-terminal devices, logic switches and other nano-electronic devices. These compounds can potentially function as active elements in electronic devices such as in self assembly monolayers (SAMs) for random-access-memory devices where data can be written, read and erased, or in sensors. Similarly, single molecules can be used as molecular wires and/or molecular switches. This invention provides a process for the synthesis or construction of supramolecular structures comprising the sequential addition of such molecules on to a solid substrate.

Accordingly, the invention provides a conducting molecule according to the Formula of I or II:

wherein R is independently selected from the group consisting of:

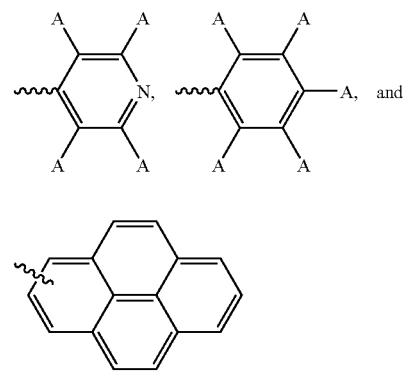

wherein A is independently selected from the group consisting of H, a $C_1$-$C_6$ alkyl group, F, —CN, SCN, $NH_2$ and —SC(O)$CH_3$, wherein at least one of F, —CN, and —SC(O)$CH_3$ is present;

B is selected from the group consisting of:

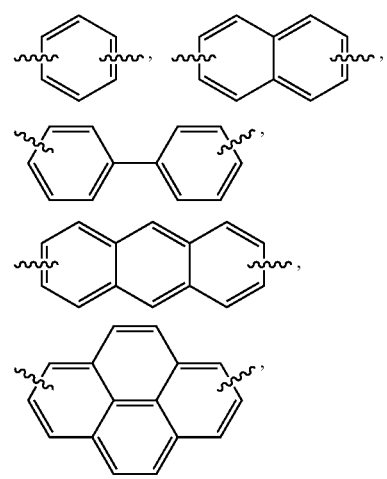

-continued

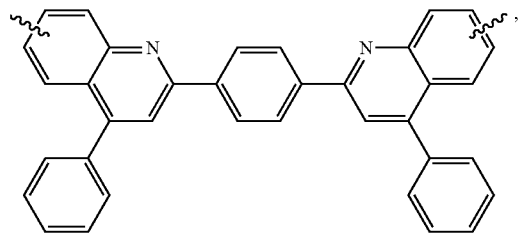

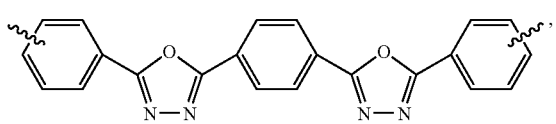

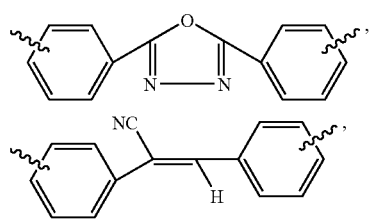

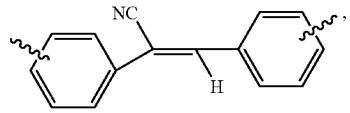

-continued

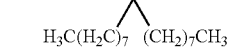

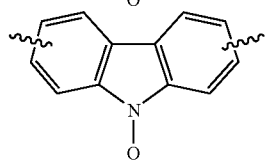

and

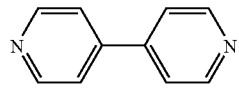

wherein B is optionally substituted with H, a $C_1$-$C_6$ alkyl group, F, —CN, —$NO_2$ and —SC(O)$CH_3$; and D can be independently selected from the group consisting of H, methyl, ethyl, propyl, isopropyl, isobutyl, t-butyl and neopentyl group and can be optionally substituted with halogen or cyano groups.

In one embodiment, the conducting molecule is selected from the group consisting of:

(a)

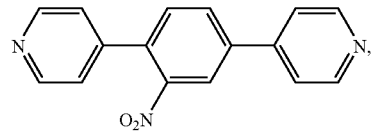

(b)

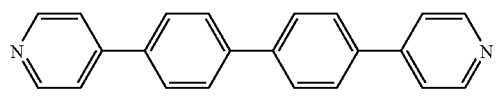

(c)

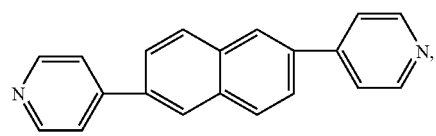

(d)

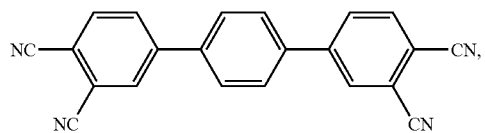

(e)

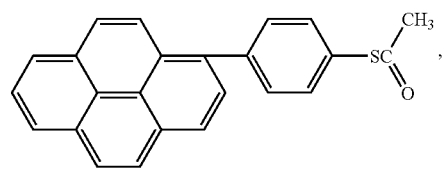

(f)

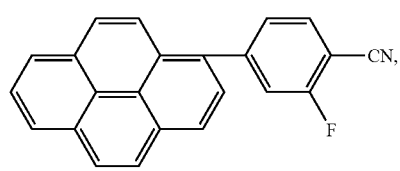

(g)

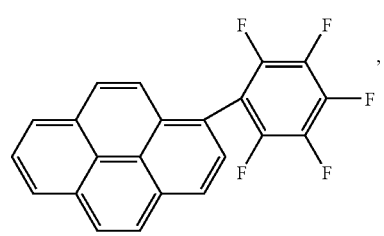

(h)

-continued
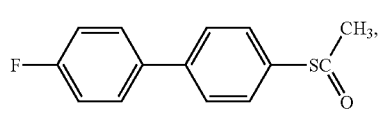
(i)
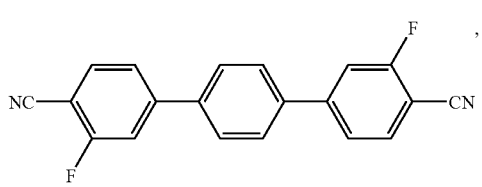
(j)
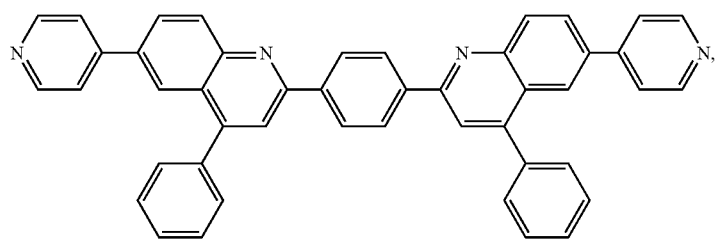
(k)
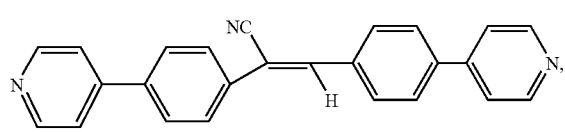
(l)
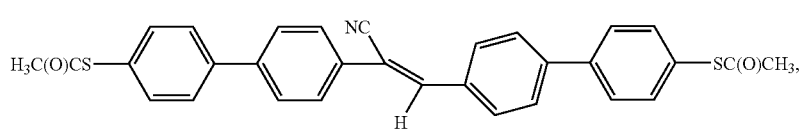
(m)
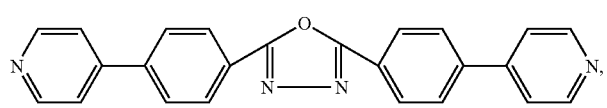
(n)
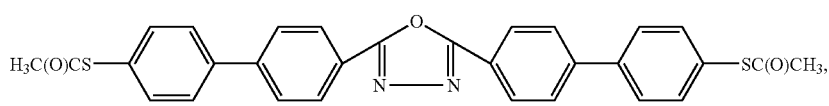
(o)
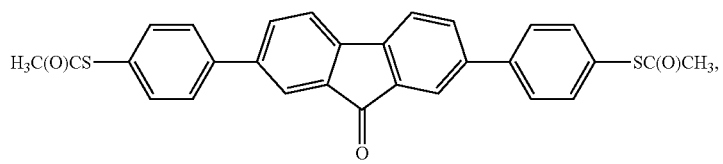
(p)
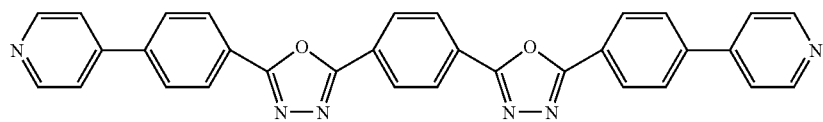
(q)
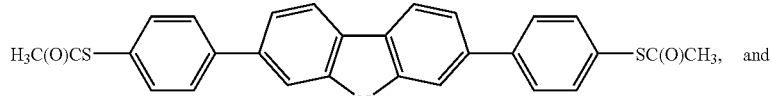
(r)
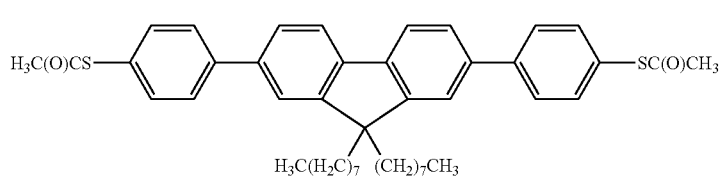
(s)
The invention also provides a molecular based memory system, molecular wire, or molecular switch, comprising a composition of the invention.
In another embodiment, the invention provides a process for synthesizing a supramolecular structure comprising the steps of:

(a) providing a first conducting molecule
(b) providing a suitable solid substrate
(c) contacting the first conducting molecule with the solid substrate wherein the conducting molecule is immobilized on the substrate (d) contacting the immobilized conducting molecule of (c) with a redox or photochemical reagent under conditions wherein the immobilized conducting molecule is activated; and
(e) contacting the activated immobilized conducting molecule of (d) with a second conducting molecule wherein molecular addition takes place and a supramolecular structure is formed.

In one embodiment, steps (d) and (e) are optionally repeated.

The invention provides a supramolecular structure useful as a sensor synthesized by the above process.

DETAILED DESCRIPTION

This invention relates to conducting molecules useful in the design, synthesis, self-assembly and processing in the solid state of organic molecules with controllable electron conducting, semiconducting or insulating properties and/or switch characteristics derived from the presence of appropriate electron active substituents placed in selected positions on aromatic and heteroaromatic structures. The present invention has met the need for functionalized molecules with the design and synthesis of novel aromatic and heteroaromatic molecules with specific substituents. The incorporation of barrier groups (—$CH_2$, cyclic, etc.) is also made possible. The molecules are robust enough to allow molecular manipulation at different temperatures and conditions. The molecular structures are versatile and allow the assembly of molecular components (possessing different terminal groups) in two or three dimensions. The resulting self-assembled monolayer can be applied via a modular chemistry approach.

For the purpose of the present invention the following definitions and abbreviations may be used for the interpretation of the claims and the specification.

"SAM" is the abbreviation for "self assembled monolayer"

"SA is the abbreviation for "self assembly". For basic reference for self-assembling; see, e.g.; "Self-Assembling Materials" by George M. Whitesides; Scientific American, September 1995

The term "conducting molecule" means any molecule that has the ability to conduct a flow of electrons from one end of the molecule to the other.

The term "supramolecular structure" means a complex of at least two, and preferably a plurality of conducting molecules. Supramolecular structures of the invention may be formed through the self-assembly of conducting molecules. "Supramolecular structures" of the invention will include the combination or linking of as few as two conducting molecules to the sequential linking of molecules in the hundreds of thousands where in practice no upper limit is unreasonable.

The term "molecular based memory system" refers to a molecule or set of molecules that have the ability to alter its conductivity by storing electrons.

The term "molecular wire" can be described as a molecular structure that allows the flow of electrons from one end to the other end of the structure. "The molecular wire" herein has two terminals for connecting to the power source or for contacting additional components of a nano-electronic device.

The term "molecular switch" is a "controllable wire" where the electron flow can be turned on and off on demand. More desirable are switches that can both switch and amplify the current. A molecule that can change its electrical conductivity by storing electrons on demand is acting as a memory device. The molecular switch can have two or three terminals. In the three terminal case the first two terminals can be considered the source and drain for the current, and the third terminal can be considered the gate, to vary the electrical conductivity of the device. Assemblies of molecular wires and switches can be interconnected in numerous manners to produce more complex circuitry for use as logic or memory or interconnection devices; see, e.g.; "Computing with Molecules" by M. Reed and J. Tour, Scientific American, June 2000, pages 86-93. "Molecular Electronics: Science and Technology", Edited by A. Aviram and M. Ratner, *Annals of the New York Academy of Sciences*, 1998, vol. 852.

The term "alligator clips" describe functional end group substituents on the structure which can be utilized as binding sites to biological molecules. These end groups could allow the construction of hybrid organic/inorganic/biological devices. Examples of such functional end groups may be one or more of SCN, $NH_2$, CN, or pyridine.

The term "solid substrate" as used herein means a material suitable for the immobilization or attachment of a conducting molecule for activation by a redox or photochemical reagent. Solid substrates suitable for such purposes are common and well known in the art and include, but are not limited to, silicon wafers, synthetic polymer supports, such as polystyrene, polypropylene, polyglycidylmethacrylate, substituted polystyrene (e.g., aminated or carboxylated polystyrene etc.); polyacrylamides; polyamides; polyvinylchlorides, glass, agarose, nitrocellulose, nylon, metal or metal oxide surfaces such as Au, Cu, Pd, Pt, Ni, Al, $Al_2O_3$, including grids or disks, carbon supports, aminosilane-treated silica, polylysine coated glass, mica, and semiconductors such as Si, Ge, and GaAs.

As used herein, "alkyl" means an alkyl group containing up to 6 carbon atoms. Common examples of such alkyl groups include methyl, ethyl, propyl, isopropyl, butyl, s-butyl, isobutyl, pentyl, neopentyl, hexyl, and cyclohexyl. The alkyl group may be linear, branched, or cyclic and can further be substituted with halogen or cyano groups. Within the context of the molecular formulae illustrated herein, the attachment points of the groups designated as designated as "R" and "B" are indicated by ⁓⁓, and unless specifically attached to a position on the ring the point of attachment can be at any open position of the designated ring.

Additionally, the compounds can potentially function as active elements in electronic devices such as in SAMs for random-access-memory devices where data can be written, read and erased, or in sensors. Similarly, single molecules can be used as molecular wires and/or molecular switches. Wires and switches are the most basic components of memory and logic devices and components comprised of the present materials will play a critical role in reducing the size of today's computer circuits.

It is an object of the present invention to provide materials that permit the control of the electronic conduction properties in aromatic and heteroaromatic building blocks linked together in configurations in which π low energy orbitals are delocalized from one end to the other end of the molecule by incorporating specific types of electron-active groups as substituents in selected positions. The aromatic and or heteroaromatic structures can be prepared by any means, but are easily synthesized via cross-coupling reactions of halogenated aromatic compounds with terminal aromatic acetylenes as is shown in the reaction schemes shown below. Various electron active, withdrawing (F, $CF_3$, $SO_2CF_3$) and donating (($N(CH_3)_2$, $N(C_2H_5)_2$) groups can be used to substitute different positions of the aromatic and heteroaromatic rings in order to vary the conduction properties and/or achieve controlled response with voltage changes. The ends of these molecules are individually functionalized with groups such as —SH, pyridine, —CN, —SCN, etc. (alligator clips) to promote the immobilization and self-assembly (SA) on a suitable substrate as discussed above. The SA is achieved either by microcontact printing or flooding the metal surfaces or both.

The nature of the contact resulting from the SA process depends on the type of the molecular fragment and the type of the metal. It could involve covalent bonding in the case of thiols on Au, surface coordination (—CN on Au), metal polarization (naphthalene on Cu), coupling of electronic states ($C_6F_5S^-$ on Cu), ionic bond (thiophene on Al).

The use of co-absorption of two types of molecules, one electron-donor and the other electron acceptor to the metal, could lead to the formation of ordered SA surface structures with both molecules in the same surface unit cell. The new molecular structures described herein combine their ability to electron conduct/insulate and/or switch with the ability to build self-assembled mono- or multi-layers and supramolecular objects that are neither mono nor layers.

The use of these alligator clips at the ends of the molecule or distributed at other locations on the molecule, are a very flexible way to interconnect these two, three or multi-terminal devices. In addition to being a manner of interconnecting or connecting these molecular or supramolecular objects, these alligator clips can also be used as the location for chemical or biological sensing activity.

The new compounds could interact with DNA by intercalating one or more aromatic groups between base pairs of the double helix. They can find use in biosensors or other biomedical applications. For basic reference for intercalating compounds; see, e.g.; R. Scott Lokey, Yan Kwok, Vladimir Guelev, Christopher J. Pursell, Laurenece H. Hurley, and Brent L. Iverson; *J. Am. Chem. Soc.*, 1997, 119, 7202-7210.

Changes in optical absorption characteristics derived from structural variations of molecular self-assemblies monitored by spectroscopic ellipsometry (SE) may be correlated with interband transitions and used to demonstrate directly the control of electronic properties.

Measurements of optical absorptions, and the ability to build complex molecules, with absorptions that are shifted to different energies, provide a method to construct supramolecular assemblies involving many different molecules with different backbones and alligator clips. Furthermore, chemistry, redox chemistry and photochemistry can be used to build up supramolecular objects sequentially. With a series of molecules, with different alligator clips, and with the same or different alligator clips on each end, one can self assemble Molecule 1 (M1), gas expose it or photoexcite it to change the unbonded alligator clip, then allow Molecule 2 (M2) to assemble on it, then photoexcite M2 or a new Molecule 3 to promote its chemical attachment to the M1/M2 built so far. This sequential build process can be a process for constructing supramolecular switches.

Thus it is within the scope of the invention to provide a process for the synthesis or construction of supramolecular structures comprising the sequential addition of molecules on to a solid substrate.

A conducting molecule is immobilized to the surface of a solid substrate in the form of mono or multi layers. It may then be contacted with a redox of photochemical reagent which results in the activation of the conducting molecule. By "activation" and "activated" it is meant that a conducting molecule is treated in a manner whereby it is disposed to react with any other conducting molecules for the generation of a supramolecular structure. The activated molecules are then contacted with additional or other conducting molecules and supramolecular structures are sequentially constructed.

The conductive molecules of the invention are expected to have metallic (ohmic) and in some cases semiconductive behavior. These behaviors lend themselves to the use of these compounds both as interconnects and as actual electronic devices (e.g. switches, logic gates). In one instance, the conductive molecules are expected to be able to link nanometer scale electronic devices together permitting the fabrication of high density electronic circuits. It is contemplated that it will be possible to array these compounds in a crossed arrangement, where the distance between adjacent molecules can be controlled by the potential difference between them, then the array could be used as a non-volatile memory device similar to that proposed by Lieber and collaborators (Rueckes T. et al. *Science*, 2000, 289, 94-97) for carbon nanotubes. Semiconducting molecules could find use in 3-terminal gated devices that can be used directly as switches, amplifiers or logic gates. Other possible applications include point sources for emission in field-emission display devices and as the conductive inclusions in conductive coatings.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Unless otherwise specified below all chemical reagents were obtained from the Sigma Chemical Co. (St. Louis, Mo.) or Aldrich (Milwaukee, Wis.).

Example 1

Synthesis of Conducting Molecules Containing Fluorene

This example demonstrates the synthesis of molecules containing fluorene units and alligator clips. The synthesis of this molecule is a multistep process as is described below.

Step-1: Preparation of 9H-fluorene-9,9-dioctyl intermediate

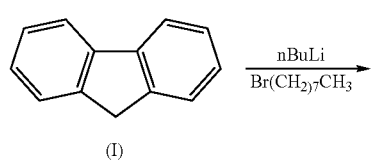

(I)

-continued

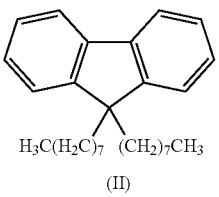

A clean, dry 500 mL 3-neck round bottom flask was charged with 8.48 g (51.1 mmoles) of fluorene (Acros Organics) and 120 mL dry tetrahydrofuran (THF) inside a dry box. 42.8 mL (107 mmoles, 2.5M solution in hexane) from Acros of n-butyl lithium (Acros Organics) was placed in an addition funnel fitted on the round bottom flask. The entire apparatus was sealed and brought outside the dry box and placed in acetone-dry ice bath. After the flask reached a temperature of −78° C., n-butyl lithium was added dropwise. The reaction was kept at −78° C. for 45 minutes. 22.7 g (117.53 moles) of octyl bromide (Aldrich) in 25 mL dry THF were added via syringe dropwise. After the addition was complete the reaction was allowed to warm up to room temperature and was kept under stirring and nitrogen purge over night. The reaction solution was distilled at 0.5 Torr at 44° C. to provide the 9,9-dioctyl derivative (II) of fluorene.

Step-2: Bromination reaction of 9H-fluorene-9,9-dioctyl intermediate

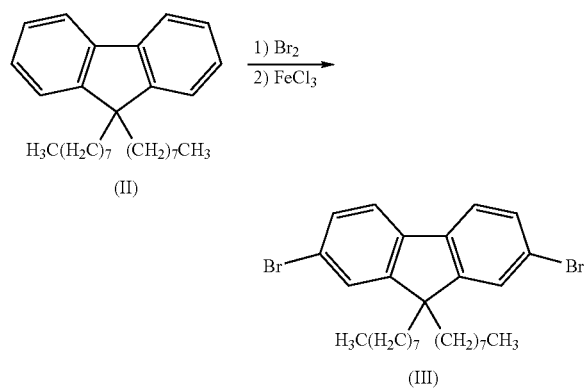

To a clean, dry 500 mL 3-neck round bottom flask the 15.01 g (38.42 mmol) of 9H-fluorene-9,9-dioctyl compound and 60 mL chloroform were added. The solution was cooled down to 0° C. in an ice bath. An Al foil was wrapped around the flask to ensure darkness during the course of the reaction. 0.098 g (0.59 mmol) of FeCl$_3$ was added to the reaction mixture followed by the addition of 4.14 mL (80.52 mmol) of Br$_2$ via a syringe. The flask was taken out from the ice bath and the reaction mixture was allowed to warm up to room temperature (r.t.) and stirred for 3 h. The reaction mixture was then poured into water and washed with sodium thiosulfate solution until the red color had dissipated. The product was then extracted with chloroform two times. The organic layers were collected, dried with MgSO$_4$ and then the solvent was pulled off using the rotary evaporator. The resulting oil was placed into an acetone/dry ice bath and the brown powder crashed out giving 20.1 g of the dibrominated intermediate 2,7-dibromo-9,9-dioctyl fluorene (III).

Step-3: Reaction of 2,7-dibromo-9,9-dioctyl fluorene with 2-isopropoxy-4,4,5,5-tetramethyl-1,3,2-dioxaborolane The title reaction was performed according to the following reaction scheme:

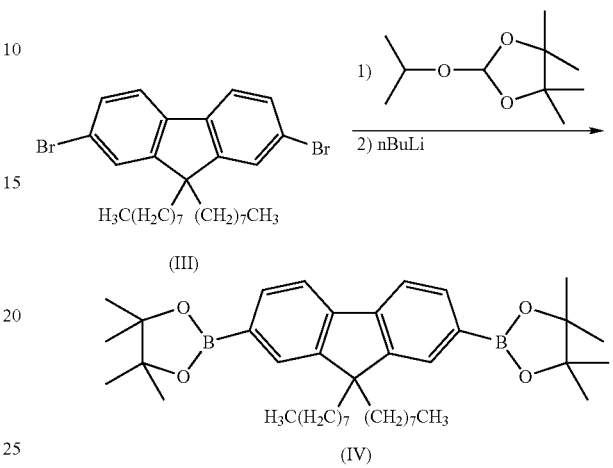

To a clean, dry 100 ml round bottom flask 70 mL of dry THF and 5 g (9.1 mmol) of 3,11-dibromo-9,9-dioctyl fluorene (III) were added. The flask was then sealed up using a rubber septum. The flask was purged with N$_2$ gas for about 15 min. The flask was cooled down to −78° C. and 7.64 mL (19.11 mL) of n-butyl lithium was added dropwise via syringe. The reaction was then allowed to warm up to 0° C. for 15 min and then cooled down −78° C. for 15 min. 4 g (21.5 mmol) of dioxaborolane reagent 2-isopropoxy-4,4,5,5-tetramethyl-1,3,2-dioxaborolane was then added via syringe very quickly and the reaction was allowed to warm up to room temperature and was stirred for 24 h. The reaction mixture was then poured into water and extracted three times with 200 mL of ether. The ethereal layers were collected, dried using MgSO$_4$ and concentrated using rotorvaporator. A dark orange oil was obtained. Chromatographic purifications were performed by flash chromatography on EM Science silica gel (230-400 mesh). The column was run using 7% ethyl acetate in hexane. The product was obtained as an orange oil.

Step-4: Synthesis of 1-bromo-4-(thioacetyl)benzene

The title compound 1-bromo-4-(thioacetyl)benzene compound was prepared as is indicated in the following reaction scheme:

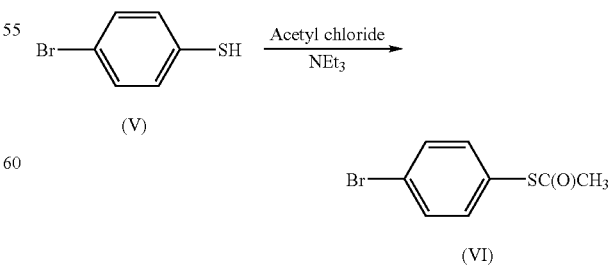

The reaction was conducted in THF using 4-bromobenzenethiol (V) as a starting compound. Into A 200 ml flask which was dried and purged with nitrogen was fitted with stirring condenser, CaCl₂ guard tube, dropping funnel. The flask was now charged with 5 g (26.5 mmol) of 4-bromobenzene thiol in 25 ml dry THF followed by 5.16 ml (3.746 g, 36.9 mmol) of triethylamine. The reaction mixture was cooled in an ice bath and a solution of 2.9 g (36.9 mmol) of acetyl chloride in 10 ml dry THF was added dropwise at 0° C. The reaction was exothermic giving yellowish brown precipitate. The reaction mixture was kept at ~0° C. (using a dry ice/acetone as cooling bath) all the time until addition was complete. After the complete addition of acetyl chloride the reaction was allowed to warm to room temperature and maintained under stirring for at least 12 hours. The reaction mixture was then filtered and the solvent removed using a rotary evaporator. The residue was purified by silica gel flash chromatography (8:2 hexane/CH₂Cl₂, 7:2 hexane/CH₂Cl₂) to provide the product 1-bromo-4-(thioacetyl)benzene (VI) as a white solid.

Step-5: Synthesis of Thioacetyl Benzene Terminated Fluorene Compound

The incorporation of terminal groups, which can be further used for attachment to metal electrodes is achieved following Suzuki Pd coupling methodologies using methods from the literature (References: Miyaura, N; Yamada, K; Suzuki, A, *Tetrahedron Lett.*, 1979, 20 (36), 3437; Miyaura, N; Suzuki A.; *Chem. Rev.*, 1995, 95, 2457; Matthew R. Netherton, Chaoyang Dai, Klaus Neuschutz and Gregory Fu, *J. Am. Chem. Soc*, 2001, 123, 10093-10100; Dai C., Fu. G, *J. Am. Chem. Soc.*, 2001, 123, 2713; A. Liltke, C. Dai, and G. Fu, *J. Am. Chem. Soc.*, 2000, 122, 4020, M. Raugler, D. Roudeau and Mario Leclerc, *Marcromolecules*, 1997, 30, 7686) as shown in the following reaction scheme. Reaction of Compound IV and Compound VI under Suzuki coupling conditions would give desired product VII.

Other terminal groups (alligator clips) such as CN, SCN, pyridine, some of them being shown as follows can be incorporated in the same manner.

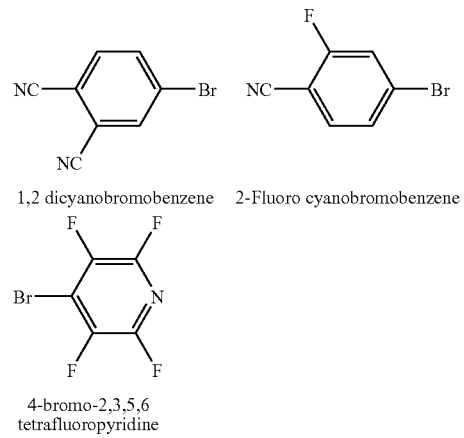

1,2 dicyanobromobenzene    2-Fluoro cyanobromobenzene 4-bromo-2,3,5,6 tetrafluoropyridine Example 2

Synthesis of Conducting Molecules Containing Fluorenone

This example demonstrates the synthesis of molecules containing fluorenone units and alligator clips. Similar synthetic procedure as described in Example 1 would be followed to introduce a fluorenone moiety instead of fluorene and to obtain the structure as shown below.

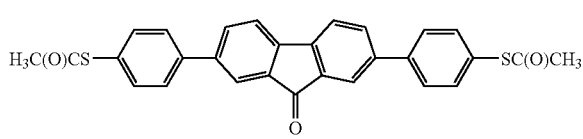

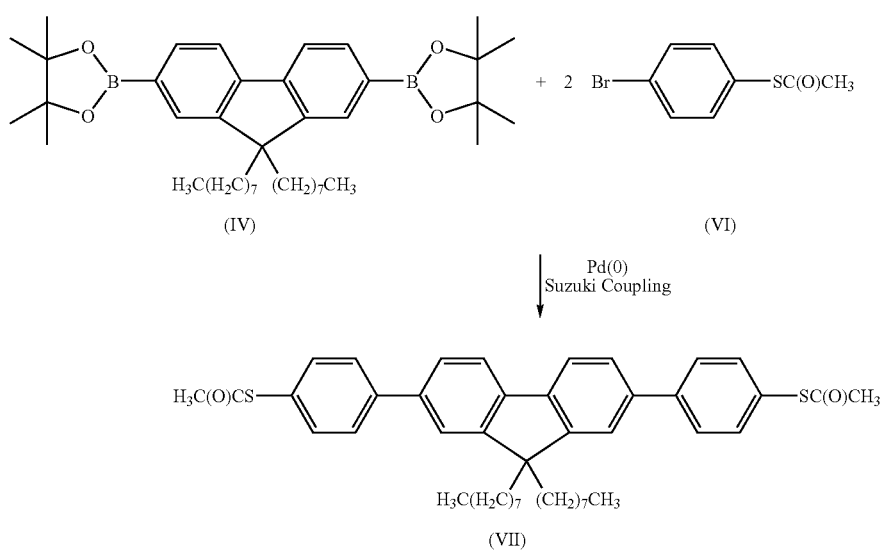

The other alligator clips that may be introduced include SCN, CN, NH$_2$, pyridine.

Example 3

Synthesis of Conducting Molecules Containing Carbazole

This example demonstrates the synthesis of molecules containing carbazole units and alligator clips.

Similar synthetic procedure as described in Example 1 would be followed to introduce a carbazole moiety instead of fluorene and to obtain the structure as shown below.

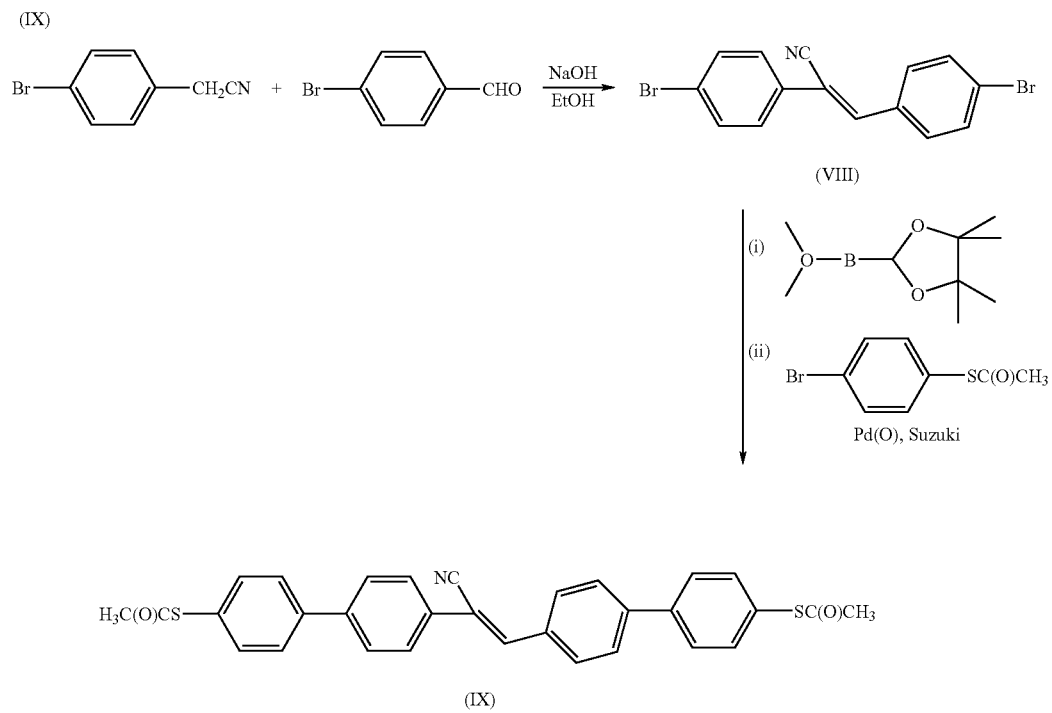

The other alligator clips that may be introduced include SCN, CN, NH$_2$, pyridine. Group "D" can be independently selected from the group consisting of H, methyl, ethyl, propyl, isopropyl, isobutyl, t-butyl and neo-pentyl group and can be optionally substituted with halogen or cyano groups.

Example 4

Synthesis of Conducting Molecules Containing Cyanovinylene

This example demonstrates the synthesis of molecules containing cyanovinylene units and alligator clips.

These compounds can be synthesized according to the following reaction scheme:

4-bromophenylacetonitrile reacts with 4-bromobenzaldehyde in an alkaline alcoholic medium to afford 1,2-bis(bromophenyl)-1-cyanovinyledene (VIII). Compound VIII is further reacted 2-isopropoxy-4,4,5,5-tetramethyl-1,3,2-dioxaborolane under conditions similar to step-3 in Example 1. The resulting product thus obtained is subjected to Suzuki coupling conditions similar to step-5 in Example 1 to obtain the desired product IX. Other alligator clips which can be introduced are CN, SCN, NH$_2$, pyridine.

Example 5

Synthesis of Conducting Molecules Containing Phenyl-1,3,4-oxadiazole

This example demonstrates the synthesis of molecules containing phenyl-1,3,4-oxadiazole units and alligator clips.

These compounds can be synthesized according to the following reaction scheme:

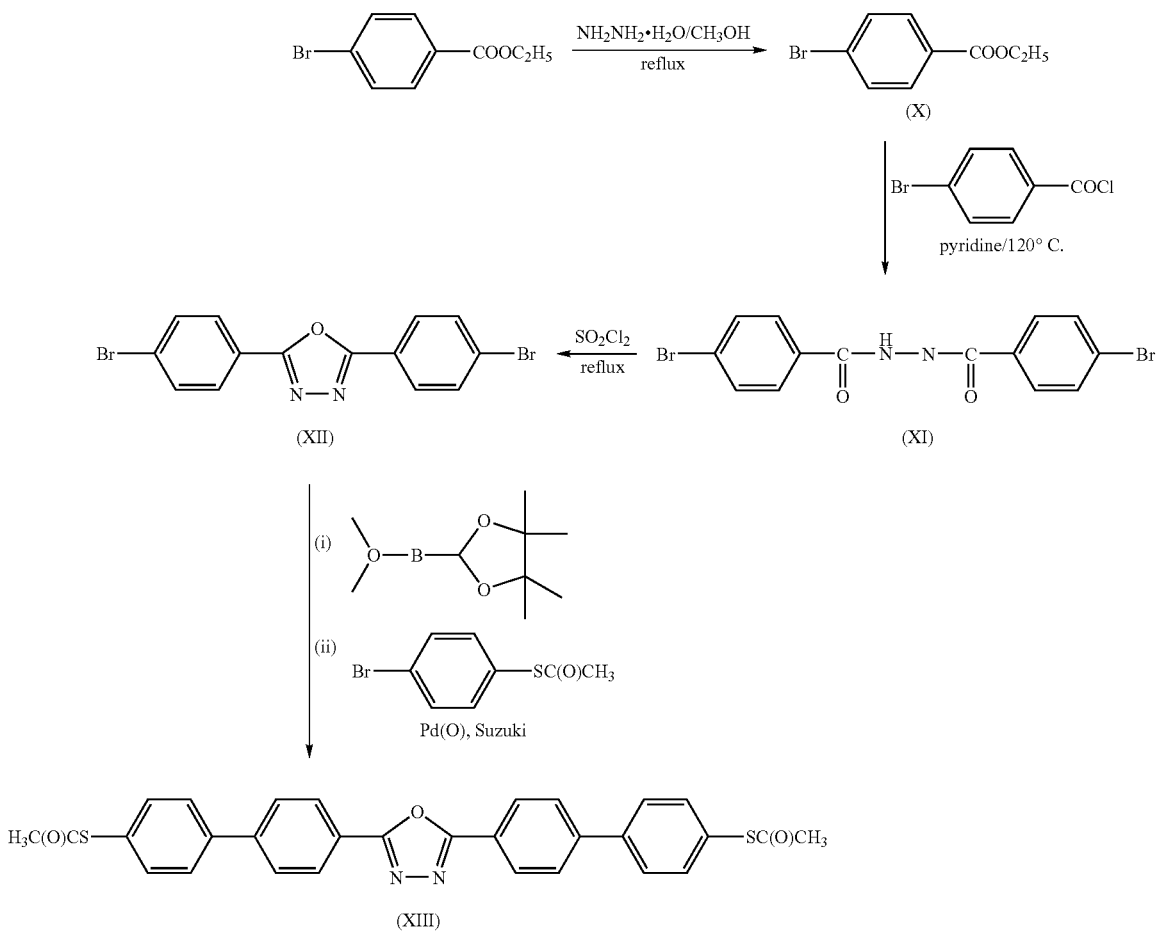

Ethyl-4-bromobenzoate is treated with hydrazine monohydrate in methanol under reflux conditions to obtain product X, 4-bromobenzoic hydrazide. Reaction of compound X with bromobenzoic acid in pyridine at 120° C. gives product XI, bis-(4-bromophenyl) hydrazine. Compound XI is then treated with sulfonyl chloride to afford 2,5-bis-(4-bromophenyl)-1,3,4-oxadiazole (Compound XII), which is further reacted 2-isopropoxy-4,4,5,5-tetramethyl-1,3,2-dioxaborolane under conditions similar to step-3 in Example 1. The resulting product thus obtained is subjected to Suzuki coupling conditions similar to step-5 in Example 1 to obtain the desired product XIII. Other alligator clips which can be introduced are CN, SCN, $NH_2$, pyridine.

Example 6

Synthesis of Conducting Molecules Containing bis[phenyl-1,3,4-2-yl]benzene-oxadiazole This example demonstrates the synthesis of molecules containing bis[phenyl-1,3,4-2-yl]benzene-oxadiazole units and alligator clips.

Step-1: Reaction of Dimethyl Terephthalate with Hydrazine Monohydrate

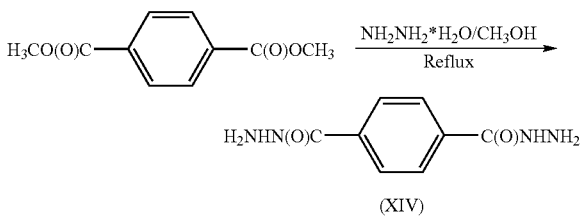

A clean, dry 500 mL round bottom flask kept inside a dry box was charged with 5 g (25.7 mmol) of dimethyl terephthalate (Aldrich) and 4.99 mL (102.98 mmol) of hydrazine monohydrate (Aldrich) in 25 mL methanol. The reaction mixture was equipped with a condenser and the entire apparatus was sealed with a septum. The flask was brought outside the box and placed under $N_2$ gas and heated to reflux for 2 hours. The heating was turned off and the reaction was allowed to stir at room temperature overnight, poured in distilled water, filtered and dried to obtain the product, Compound XIV.

2: Compound XIV can be further reacted with bromobenzoic chloride to obtain a dibromo derivative (XV)

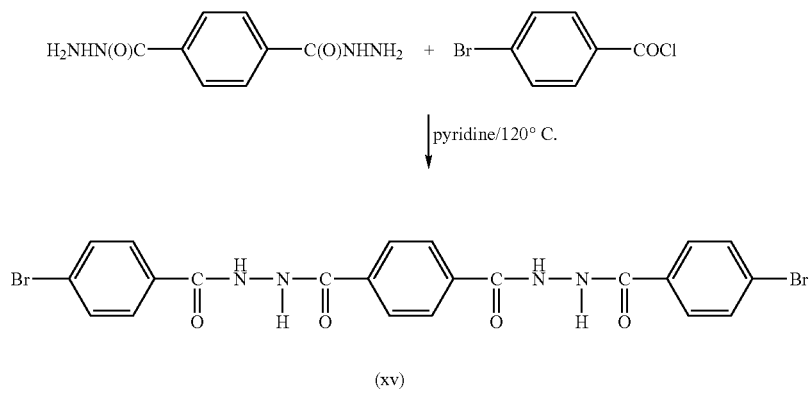

(xv)

3) The dibromo derivative XV, is reacted with sulfonyl chloride under reflux conditions to obtain the 1,4-bis[(4-bromophenyl)-1,3,4-2-yl]benzene-oxadiazole (XVI) as is indicated in the following reaction scheme:

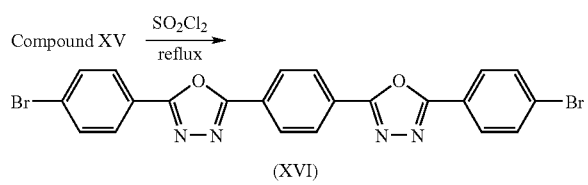

(XVI)

4) Compound XVI can be further reacted 2-isopropoxy-4,4,5,5-tetramethyl-1,3,2-dioxaborolane under conditions similar to step-3 in Example 1. The resulting product thus obtained is subjected to Suzuki coupling conditions similar to step-5 in Example 1 to obtain the desired product XVII. Other alligator clips which can be introduced are CN, SCN, $NH_2$, pyridine.

Example 7

Prophetic

Self-Assembly and Spectroscopic Ellipsometry Measurement

Differences in electrical conducting properties of the conducting molecules of the invention may be detected by measuring various spectroscopic and ellipsometric parameters. This example demonstrates various differences in those parameters in the compounds made and disclosed herein, indicating a variation in their electrical conduction. The compounds used in this example are drawn from the previous examples. These compounds can be subjected to self-assembly chemistry on gold, and silicon substrates. The gold substrates are thin films depositions on Si wafers with a Ti layer for adhesion. The as-received gold substrate is further cleaned in UV/ozone plasma cleaner. The self-assembly is then prepared on the substrates using the procedures described in C. Zhou, et al, *Appl. Phys. Lett.*, 1997, 71, 611; M. T. Cygan et al, *J. Am. Chem. Soc.*, 1998, 120, 2721-2732; and J. Chen et al,

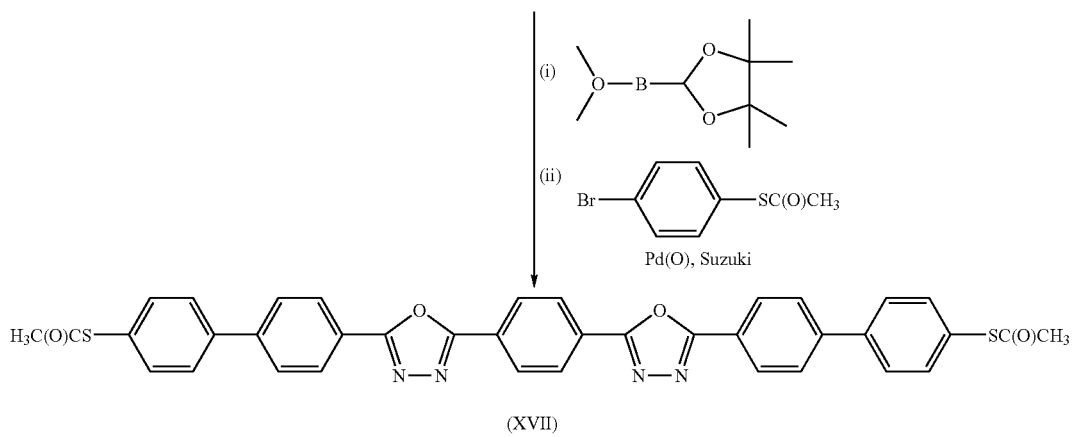

(XVII)

Science, 1999, 286, 1550. Optical properties (index of refraction, "n" and extinction coefficient, "k") are determined from variable angle spectroscopic ellipsometry (VASE) at three incident angles covering the wavelength range from 143-800 nm, corresponding to an energy range of 1.5-8.67 eV. The samples for ellipsometry consisted of the self-assembled molecules on a gold-coated silicon wafer substrate. The VASE ellipsometer has been manufactured by J. A. Woollam Company, 645 M Street, Suite 102, Lincoln, Nebr. 68508 USA. Optical constants are fit to these data simultaneously, using an optical model of the film on the substrate. This method is described in O. S. Heavens, Optical Properties of Thin Solid Films, pp. 55-62, Dover, N.Y., 1991.

Two approaches are used in the ellipsometric modeling: a Cauchy (C) or a Spectral Cauchy (SC). In the Cauchy model fits, the index of refraction (n) of the self-assembled molecules is presumed to have a fixed value. Most typically n was set equal to 1.45, and then only the thickness of the self-assembled molecules was fitted. In the SC approach, the thickness found with the Cauchy model is then fixed and the optical constants, the complex index of refraction n+ik, is then fitted as a function of wavelength. This allows the determination of the spectral variation of the index of refraction and the extinction coefficient and gave a direct insight into the optical absorptions and electronic transitions in the self-assembled molecules.

What is claimed is:

1. A conducting molecule according to Formula II:

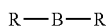

II wherein R is independently selected from the group consisting of:

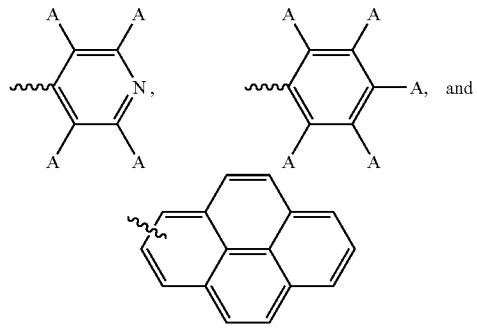

wherein A is independently selected from the group consisting of H, a $C_1$-$C_6$ alkyl group, F, —CN, SCN, $NH_2$ and —SC(O)$CH_3$, wherein at least one of F, —CN and —SC(O)$CH_3$ is present;

and wherein B is:

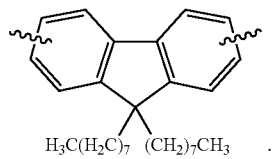

2. A conducting molecule selected from the group consisting of:

(a)

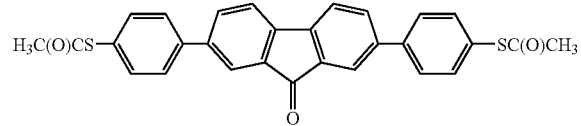

and (b)

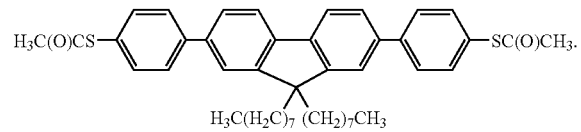

3. A conducting molecule according to Formula II:

II wherein R is independently selected from the group consisting of compounds:

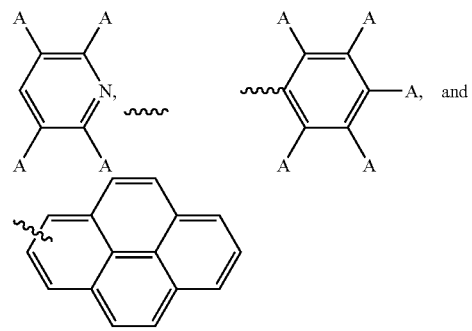

wherein, for compound

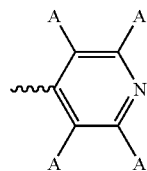

A is independently selected from the group consisting of H, a $C_1$-$C_6$ alkyl group, F, —CN, SCN, $NH_2$ and —SC(O)$CH_3$, wherein at least one of F, —CN, and —SC(O)$CH_3$ is present;

and for compound

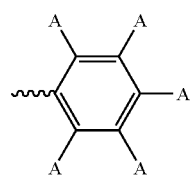

A is independently selected from the group consisting of H, a $C_1$-$C_6$ alkyl group, —CN, SCN, $NH_2$ and —SC(O)$CH_3$, wherein at least one of —CN, and —SC(O)CH₃ is present; and
wherein, B is selected from the group consisting of:
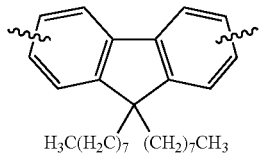 and
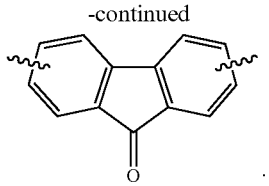
* * * * *